(12) United States Patent
Honkura

(10) Patent No.: US 11,009,566 B2
(45) Date of Patent: May 18, 2021

(54) THREE-DIMENSIONAL MAGNETIC FIELD DETECTION ELEMENT AND THREE-DIMENSIONAL MAGNETIC FIELD DETECTION DEVICE

(71) Applicant: ASAHI INTECC CO., LTD., Aichi (JP)

(72) Inventor: Yoshinobu Honkura, Chita-gun (JP)

(73) Assignee: ASAHI INTECC CO., LTD., Seto (JP)

( * ) Notice: Subject to any disclaimer, the term of this patent is extended or adjusted under 35 U.S.C. 154(b) by 169 days.

(21) Appl. No.: 16/439,699

(22) Filed: Jun. 13, 2019

(65) Prior Publication Data
US 2019/0310324 A1 Oct. 10, 2019

Related U.S. Application Data

(63) Continuation of application No. PCT/JP2017/044968, filed on Dec. 14, 2017.

(30) Foreign Application Priority Data

Dec. 15, 2016 (JP) .............................. JP2016-242816

(51) Int. Cl.
G01R 33/02 (2006.01)
H01L 43/00 (2006.01)
A61M 25/01 (2006.01)

(52) U.S. Cl.
CPC ......... *G01R 33/0206* (2013.01); *G01R 33/02* (2013.01); *H01L 43/00* (2013.01); *A61M 25/0127* (2013.01)

(58) Field of Classification Search
CPC ................................................ G01R 33/0206
See application file for complete search history.

(56) References Cited

U.S. PATENT DOCUMENTS 7,298,140 B2 * 11/2007 Honkura ................ G01R 33/02
324/247
7,509,748 B2 * 3/2009 Xue ........................ G01C 17/28
33/355 R (Continued)

FOREIGN PATENT DOCUMENTS

JP 2009-216390 A 9/2009
JP 2014-153309 A 8/2014
JP 2016-151413 A 8/2016

OTHER PUBLICATIONS

International Search Report and Written Opinion dated Mar. 20, 2018 for PCT/JP2017/044968 filed on Dec. 14, 2017, 8 pages including English Translation of the International Search Report.

(Continued)

*Primary Examiner* — Walter L Lindsay, Jr.
*Assistant Examiner* — Milton Gonzalez
(74) *Attorney, Agent, or Firm* — Xsensus LLP

(57) ABSTRACT

The invention relates to a three-dimensional magnetic field detection device (1) which comprises three soft-magnetic bodies (21, 22) and a magnetic field detection element (3, 12, 13, 14) comprising three GSR elements. For three axial directions that are orthogonal to each other at an origin point that is the center point of measurement, the invention measures, for a first axial direction, a first-axial-direction magnetic field using two elements sandwiching the origin point, measures, for a second axial direction, a second-axial-direction magnetic field through disposing one element at the position of the origin point, and measures, for a third axial direction, a third-axial-direction magnetic field through combining the two elements for the first axial direction and the three soft-magnetic bodies and forming two crank-shaped magnetic circuits having point symmetry.

6 Claims, 7 Drawing Sheets

(56) References Cited

U.S. PATENT DOCUMENTS

| | | | | |
|---|---|---|---|---|
| 7,535,221 B2* | 5/2009 | Satoh | ............... | G01R 33/0206 |
| | | | | 324/253 |
| 8,076,930 B2* | 12/2011 | Chang | ................... | G01R 33/04 |
| | | | | 324/247 |
| 8,339,132 B2* | 12/2012 | Honkura | ............. | G01R 33/063 |
| | | | | 324/244 |
| 8,455,962 B2* | 6/2013 | Honkura | ............... | G01R 33/18 |
| | | | | 257/414 |
| 8,713,809 B2* | 5/2014 | Ohmori | ................ | G01R 33/05 |
| | | | | 33/361 |
| 9,234,946 B2* | 1/2016 | Itoi | ...................... | G01C 17/30 |
| 9,658,298 B2* | 5/2017 | Cai | ...................... | G01R 33/00 |
| 10,620,276 B2 | 4/2020 | Shimoto et al. | | |
| 2016/0054352 A1 | 2/2016 | Kang et al. | | |

OTHER PUBLICATIONS

Maenaka et al., "Integrated three-dimensional magnetic sensor", The transactions of the Institute of Electrical Engineers of Japan, vol. 109, No. 7, Chapter 3, Jul. 1989, pp. 483-490.

* cited by examiner

THREE-DIMENSIONAL MAGNETIC FIELD DETECTION ELEMENT AND THREE-DIMENSIONAL MAGNETIC FIELD DETECTION DEVICE

CROSS-REFERENCE TO RELATED APPLICATIONS

This application is a continuation of International Patent Application No. PCT/JP2017/044968, filed on Dec. 14, 2017, which claims the benefit of Japanese Patent Application No. 2016-242816, filed on Dec. 15, 2016, the entire contents of each are incorporated herein by reference.

TECHNICAL FIELD OF THE INVENTION

The present invention relates to a triaxial magnetic sensor used as an azimuth sensor and the like, and particularly to a three-dimensional magnetic field detector including a three-dimensional magnetic field detection device having a function of detecting a magnetic field in three, x-axial, y-axial and z-axial directions, which device, as being realized on a single substrate, is reduced in height and cross-sectional area while maintaining such basic performances of a magnetic sensor as a high sensitivity, a low noise, and a wide measurement range.

BACKGROUND ART

A triaxial magnetic sensor is adapted to measure the terrestrial magnetism vector with three magnetic sensor elements for the x-axial, y-axial and z-axial directions combined with an integrated circuit, and calculates the azimuth from the value of the measured vector. Such triaxial magnetic sensor is combined with an acceleration sensor or a vibratory gyro sensor and, as such, used as a three-dimensional azimuth meter in a variety of apparatuses, such as an electronic compass, a smartphone, a tablet terminal, a remote controller for Internet TV, a motion game machine, and a motion capturing apparatus. In recent years, reduction in size and thickness is eagerly required of the above apparatuses, as well as further improvement in sensitivity, noise reduction, and in measurement range. As smartphones are reduced in thickness, in particular, azimuth sensors are required to have a height 40% or more reduced from a conventional height of 1.0 mm, a height of 0.6 mm for instance, and a size 50% or more reduced from a conventional size of 2.0 mm square, a size of 1.5 mm square for instance. With respect to the noise, the required magnitude is 1 mG or less, that is to say, ten-time improvement of a conventional noise of 10 mG or less is required.

In an azimuth sensor, a Hall element, an MR element, a magneto-impedance (abbreviated to MI) element, a GHz spin rotation (abbreviated to GSR) element or the like is used as an element for magnetic field detection. Generally, three elements, an x-axial one, a y-axial one and a z-axial one, are used to measure the strength of an x-axial magnetic field vector component Hx, a y-axial magnetic field vector component Hy and a z-axial magnetic field vector component Hz, respectively. If use is made of Hall elements detecting a magnetic field in the direction perpendicular to a device face, the z-axial element needs to be positioned on the device face while the x-axial and y-axial elements need to be mounted upright on the sensor substrate. In the case of MR elements, MI elements and the like detecting a magnetic field parallel to a device face, the x-axial and y-axial elements need to be positioned on the device face while the z-axial element needs to be mounted upright (in the z-axial direction) on the sensor substrate. A problem with the increase of sensor height thus arises as long as three elements are used as assembled. As an example, Patent Literature 1 discloses an assembled triaxial magnetic sensor using MI sensors.

Note that discussion herein is focused on MI elements and GSR elements because Hall elements are of a high noise and hard to improve in performance.

With respect to the problem as above, Patent Literature 2 discloses an integrated, three-dimensional magnetic detection device including x-axial elements and y-axial elements arranged on a single substrate, and having the function of z-axial element.

The disclosed device is the three-dimensional magnetic detection device, in which a pair of x-axial elements, namely an X1 axial element and an X2 axial element, and a pair of y-axial elements, namely a Y1 axial element and a Y2 axial element, are positioned in the x-axial and y-axial directions on a substrate face, respectively, so as to shape a cross, and a permalloy core rod is provided below the center of crossing.

The three-dimensional magnetic detection device as above detects the magnetic field in the x-axial direction by adding the output from the X1 axial element and the output from the X2 axial element, detects the magnetic field in the y-axial direction by adding the output from the Y1 axial element and the output from the Y2 axial element, and detects the magnetic field in the z-axial direction by deflecting the magnetic field in the z-axial direction with the permalloy core rod to generate a deflected component in a plane direction and adding the deflected component to the difference between the output from the X1 axial element and the output from the X2 axial element and the difference between the output from the Y1 axial element and the output from the Y2 axial element, so as to obtain a three-dimensional magnetic field vector.

The force of a permalloy core rod that should cause the magnetic field in the z-axial direction to be deflected in a plane direction, however, is very weak. Consequently, the three-dimensional magnetic detection device needs a longer permalloy rod with a larger diameter and has to have a thickness of 0.5 mm or more, which makes the device unpractical.

Patent Literature 3, in which MI element-type elements are further improved in size, discloses the three-dimensional magnetic field detection device, in which two soft magnetic bodies are each provided at an end of an MI element, one above one end and the other below the other end, that is to say, a magnetic circuit in crank form is formed using two soft magnetic bodies and one element, so as to allow an effective detection of the magnetic field in the z-axial direction.

In the configuration of the disclosed device, four MI elements are arranged on a flat face of a substrate around the origin of the substrate so that two of them may be positioned in the x-axial direction and the rest two may be on the y-axis crossing the x-axis. In the substrate under the origin, and above ends of the four MI elements, which ends are each opposite to the origin, soft magnetic bodies are positioned, so as to form a magnetic circuit composed of magnetic field detecting elements and soft magnetic bodies. Such configuration has brought about a three-dimensional magnetic field detection device having a width of 0.7 mm, a length of 0.7 mm, and a thickness of 0.3 mm.

Still more reduction in size and thickness, however, is required for the purpose of applying a recent azimuth sensor to a wearable computer, the tip of a guide wire of a medical catheter, and so forth.

The x-axial magnetic field component and the y-axial magnetic field component are each obtained by adding the measured values from the right and left magnetic field detecting elements, and the z-axial magnetic field component is obtained by calculating the difference between the measured values from the right and left magnetic field detecting elements. It is therefore required that the right and left magnetic field detecting elements are of the same value with respect to one and the same direction and, for magnetic fields in opposite directions, output the values which are the same in magnitude but opposite in sign, so that structural symmetry is very important. As magnetic field detecting elements are more sophisticated, even a slight difference between the right and left elements is more critical.

CITATION LIST

Patent Literature

Patent Literature 1: WO 2005/008268
Patent Literature 2: WO 2010/110456
Patent Literature 3: JP 2014-153309 A

SUMMARY OF THE INVENTION

Problems to be Solved by the Invention

In view of the technical background as described above, the present inventor focused on the GSR sensor as recently developed. The arrangement of magnetic field detecting elements on a substrate face, the magnetic field-collecting structure for the magnetic field in the z-axial direction, and the positioning of soft magnetic bodies were studied not only so as to improve the magnetic field detecting capability but review the size of a three-dimensional magnetic field detection device, the present invention having thus been made.

Means for Solving the Problems

The present inventor investigated a further reduction in size of the three-dimensional magnetic field detection device as disclosed in Patent Literature 3 and, as a result, devised a structure using three magnetic field detecting elements instead of four. The structure makes it possible to measure the magnetic field in a first axial direction by two elements 12 and 13 for the first axial direction, measure the magnetic field in a second axial direction by a single element 14 positioned at the origin, and measure the magnetic field in a third axial direction by combining the two elements for the first axial direction with three soft magnetic bodies to point-symmetrically form two magnetic circuits, each in crank form, whereupon the first, second and third axial directions are orthogonal to one another at the origin as the center of measurement.

The magnetic field Hx in the x-axial direction was obtained from the mean of the measured values from the elements 12 and 13, respectively. The magnetic field Hy in the y-axial direction was obtained from the measurement by the element 14. The magnetic field Hz in the z-axial direction was obtained from the mean of differences between the measured values from the elements 12 and 13, respectively. For the purpose of reduction in size, elements with smaller lengths were employed as the elements 12 and 13 so as to reduce the length in the longitudinal direction so that the sensitivity as a summed output of the two elements 12 and 13 might be the same as the sensitivity of the element 14 as a reference. The elements 12 and 13 with smaller lengths allowed the magnetic circuits to have a smaller magnetic resistance, and modification of the size of soft magnetic bodies allowed not only the equalization of the detection sensitivity in the z-axial direction to the sensitivity of the element 14 but the reduction in size in the thickness direction.

As a result of using high-sensitive GSR elements to reduce the device length, the entire device was reduced in size.

Effects of the Invention

According to the invention, use of GSR elements allows a three-dimensional magnetic field detection device to have even reduced size and thickness while maintaining such basic performances as a high sensitivity, a low noise and a wide measurement range. The decrease in number of magnetic field detecting elements leads to cost reduction. In addition, it is possible to reduce the size and thickness of a three-dimensional magnetic field detector.

DESCRIPTION OF EMBODIMENTS

Figure 1:
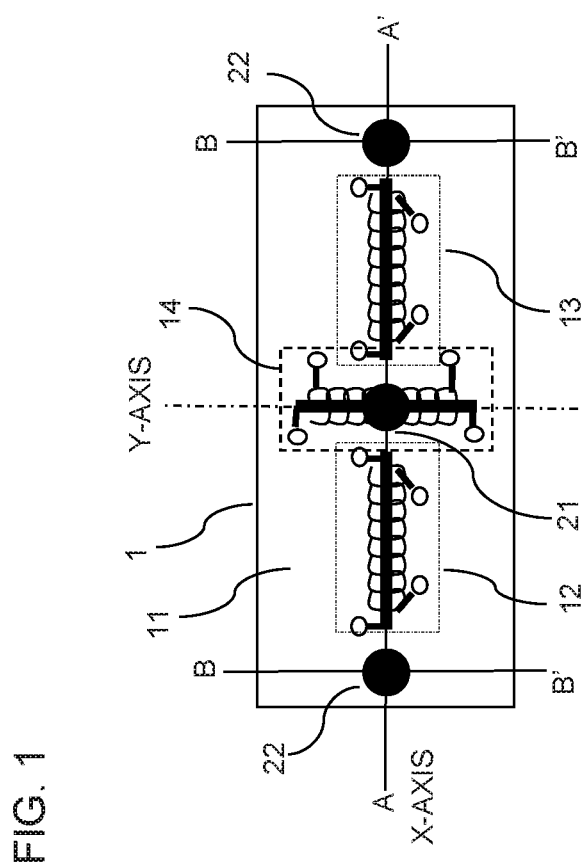
FIG. 1 is a plan view of a three-dimensional magnetic field detection device according to Embodiment 1.

According to the invention, a three-dimensional magnetic field detection device includes magnetic field detecting elements configured to detect a magnetic field in a direction parallel to a face of a substrate and soft magnetic bodies configured to collect and radiate a magnetic field orthogonal to the face of the substrate. An axis extending in a first axial direction on the face of the substrate, an axis extending in a second axial direction orthogonal to the first axial direction, and an axis extending in a third axial direction orthogonal to the face of the substrate cross one another at the origin as the center of measurement of the magnetic field on the face of the substrate. The magnetic field detecting elements are so arranged on the substrate that two of the magnetic field detecting elements are positioned in the first axial direction point-symmetrically with respect to the origin set as the center of symmetry and one of the magnetic field detecting elements is positioned in the second axial direction point-symmetrically with respect to the origin as the center of symmetry, and the soft magnetic bodies are positioned above the origin and below ends of the two of the magnetic field detecting elements positioned in the first axial direction, which ends are each opposite to the origin. A magnetic circuit including two of the magnetic field detecting elements and three of the soft magnetic bodies is formed in the first axial direction.

The three-dimensional magnetic field detection device includes three magnetic field detecting elements for detecting a magnetic field in the direction parallel to a substrate face, and three soft magnetic bodies.

The magnetic field detecting elements are each composed of an amorphous wire as a magnetosensitive body, a detecting coil surrounding the amorphous wire, terminals at both ends of the amorphous wire and of the detecting coil, electrode pads for bonding the terminals to one another or to an external integrated circuit, and a wiring between the terminals and the electrodes.

The diameter of the amorphous wire is 15 μm or less, preferably 10 μm or less. The periphery of the amorphous wire is preferably coated with an insulating material, glass for instance. The amorphous wire and the detecting coil are easy to insulate from each other, and the gap between them can be reduced to decrease the inner diameter of the coil.

The inner diameter of the detecting coil is 30 μm or less, preferably 20 μm or less. The reduction in inner diameter of the detecting coil improves the sensitivity. The coil pitch is 5 μm or less, preferably 3 μm or less. If the coil pitch falls within such range, the coil turn number per unit length can be increased, leading to the reduction in length and size of the magnetic field detecting element.

The arrangement of the three magnetic field detecting elements on a face of the substrate is carried out as follows.

On a face of the substrate, the center of measurement of magnetic fields parallel to the face of the substrate is defined to be the origin. Three axes (x-axis, y-axis, and z-axis) extending in a first axial direction (x-axial direction) on the face of the substrate, in a second axial direction (y-axial direction) orthogonal to the first axial direction (x-axial direction), and in a third axial direction (z-axial direction) orthogonal to the face of the substrate, respectively, pass through the origin to cross one another.

Assuming that the x-axis extends in the length direction of the substrate, the magnetic field detecting elements 12 and 13 are positioned point-symmetrically with respect to the origin set as the center of symmetry. Also, assuming that the y-axis extends in the width direction, the magnetic field detecting element 14 is positioned point-symmetrically with respect to the origin set as the center of symmetry.

As a result of using a single element for the detection of the magnetic field in the y-axial direction and point-symmetrically positioning the element, the three-dimensional magnetic field detection device can have such a size in the width direction as reduced to one third.

The soft magnetic bodies form two magnetic circuits in crank form along with the elements 12 and 13 as arranged on the substrate. The soft magnetic bodies as such collect the magnetic flux in the z-axial direction and cause the collected magnetic flux to flow through the magnetic wires in the elements. Then, the soft magnetic bodies on both sides radiate the magnetic flux, to thereby allow the detection of the strength of the magnetic field in the z-axial direction. The soft magnetic body to be used is not limited in material or form as long as a magnetic circuit can be formed with the soft magnetic body. More preferred is a soft magnetic body of a higher permeability that is more effective at collecting a magnetic field. The shape of the soft magnetic body is preferably such that the demagnetizing factor is reduced, and magnetization is effectively achieved by the magnetic field in the z-axial direction.

In view of the ease of production, the aspect ratio (H/D) of the soft magnetic body, which is determined as the ratio of the height H to the diameter (diameter-equivalent size for an elliptical shape) D, is preferably 1 or less.

The single soft magnetic body above the origin may be positioned below the origin and the two soft magnetic bodies below the ends each opposite to the origin may be positioned above the ends as long as the magnetic circuits as above are formed so as to allow the detection of the magnetic field in the z-axial direction.

The soft magnetic bodies are preferably so arranged that the magnetic circuits are likely to be formed effectively.

For instance, a pole face of a soft magnetic body and an amorphous wire end are made as close as possible to each other, to thereby reduce the resistance of a magnetic circuit. The size of a soft magnetic body as represented by the cross-sectional area and the thickness is relative to the length or diameter of a magnetic field detecting element. Preferably, a soft magnetic body has a larger thickness as the length of a magnetic field detecting element is increased.

Within the gist of the present invention, the arrangement of the x-axial elements and the y-axial element or the soft magnetic bodies is preferably such that the two axes are perpendicular to each other. If the angle as formed between the axes deviates from a right angle by certain degrees, an appropriate correction calculation in response to the angular deviation can be performed on the outputs of the magnetic field detecting elements so as to address the deviation.

In the three-dimensional magnetic field detection device of the present invention, the two soft magnetic bodies as positioned below the ends of the magnetic field detecting elements in the first axial direction are each located on the surface of a machined end face machined perpendicularly to the substrate face.

The substrate, which includes the soft magnetic bodies as located at the ends of the magnetic field detecting elements in the x-axial direction, or longitudinal direction, is machined downwards with respect to the substrate face, so that end portions including no magnetic field detecting elements are removed, and the soft magnetic bodies constitute the surfaces of machined end faces. As a result, the three-dimensional magnetic field detection device is reduced in length. Removal of the magnetic bodies by half or so may lead to the deterioration of magnetic field-collecting function. In that case, the cross-sectional area of a soft magnetic body is increased. If the cross section is enlarged in the width direction to make it elliptical, the reduction in length of the three-dimensional magnetic field detection device is less affected.

The three-dimensional magnetic field detection device of the present invention has a length of 0.6 mm or less, a width of 0.3 mm or less, and a thickness of 0.15 mm or less.

Consequently, the inventive device not only meets the expectation of use for a smartphone or wearable computer but can be incorporated into the tip of a guide cable of a medical catheter, for instance.

The three-dimensional magnetic field detector of the present invention includes the magnetic field detection device of the present invention and an integrated circuit chip bonded together.

In the three-dimensional magnetic field detector of the present invention, a magnetic field detection device for detecting three axial magnetic fields is reduced in size and thickness by forming magnetic circuits with the x-axial elements and y-axial element as mounted on a substrate and with the x-axial elements and the soft magnetic bodies, so as to detect the magnetic field in the z-axial direction. In addition, a total reduction in size or thickness is achieved by the bonding of the integrated circuit chip.

The three-dimensional magnetic field detection device of the present invention and the integrated circuit may be bonded together through wire bonding. In that case, however, an extra area or height for wire bonding is required.

For this reason, it is desirable for the promotion of a total reduction in size or thickness to electrically bond the three-dimensional magnetic field detection device and the integrated circuit together by stacking the three-dimensional magnetic field detection device and the integrated circuit and bonding them to each other with a pad.

EXEMPLIFIED EMBODIMENTS

In the following, exemplified embodiments of the invention are described in reference to the accompanying drawings.

Exemplified Embodiment 1

Figure 2:
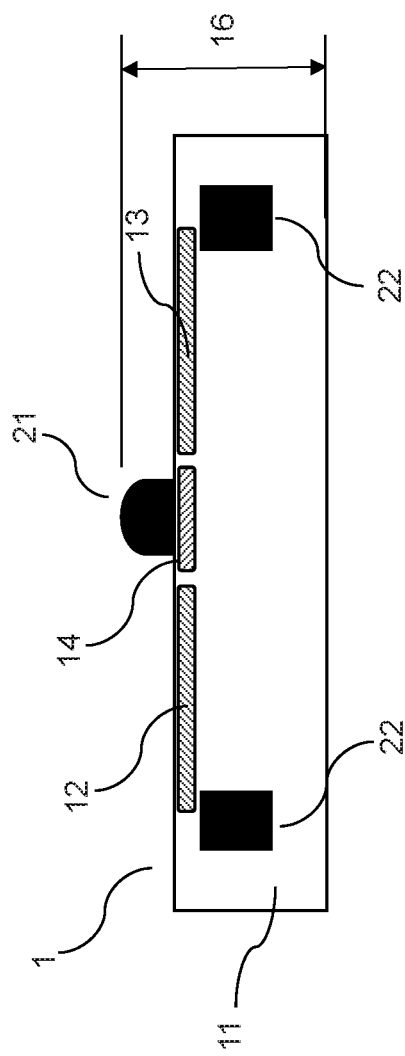
FIG. 2 is a cross-sectional view of the three-dimensional magnetic field detection device according to Embodiment 1, taken along line A-A' in the plan view (FIG. 1).
Figure 3:
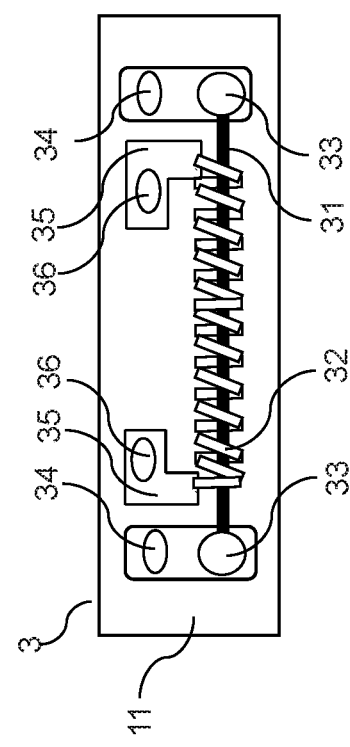
FIG. 3 is a schematic plan view showing a basic structure of a GSR element according to Embodiment 1.
Figure 4:
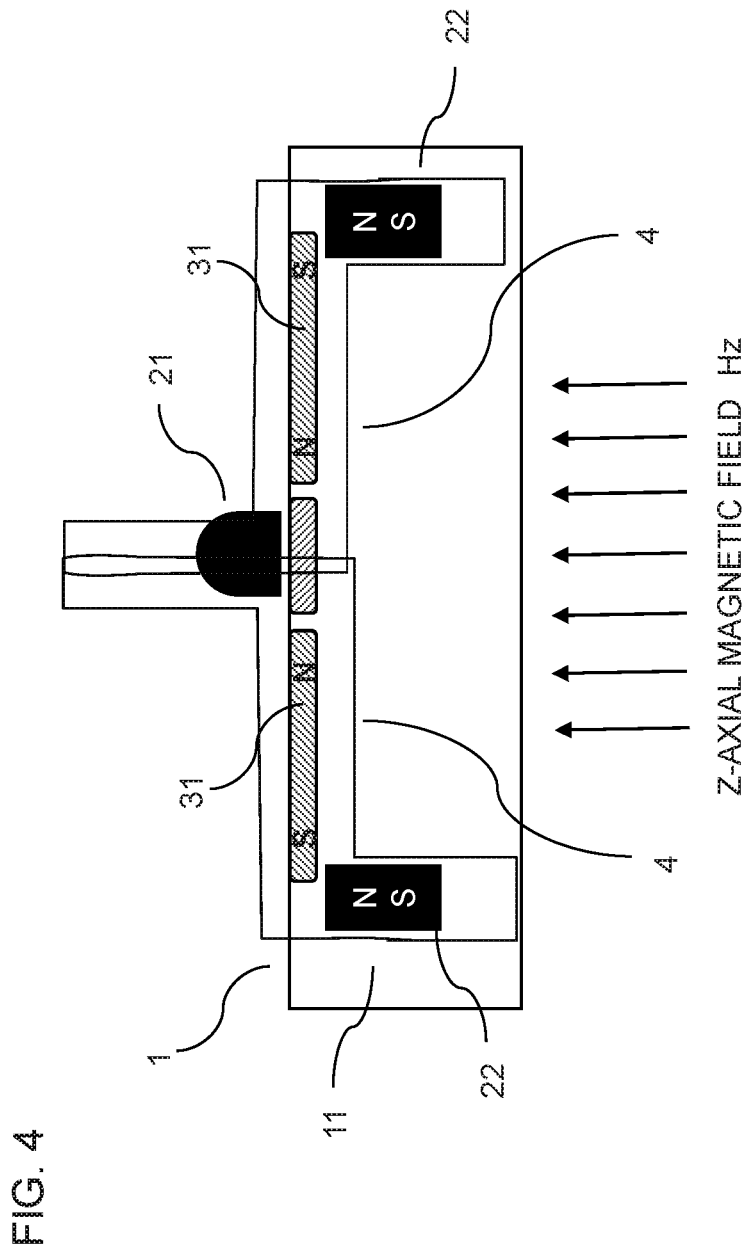
FIG. 4 is a schematic diagram showing magnetic circuits in crank form according to Embodiment 1.

A three-dimensional magnetic field detection device 1 according to Example 1 is shown in FIG. 1. FIG. 1 is a plan view of the three-dimensional magnetic field detection device, and FIG. 2 is a cross-sectional view taken along line A-A' in FIG. 1. FIG. 3 is a plan view showing a basic structure of a GSR element.

The three-dimensional magnetic field detection device 1 includes three GSR elements 3 each capable of detecting a micromagnetic field such as terrestrial magnetism, and three soft magnetic bodies 21 and 22 each having magnetic field-collecting and -radiating functions.

Of the GSR elements, two are shown as an X1 element 12 and an X2 element 13 located on the x-axis on a substrate face, and one is shown as a Y element 14 located on the y-axis. The x-, y- and z-axes are orthogonal to one another at the origin, and the X1 element 12 and the X2 element 13 are point-symmetrically positioned with respect to the origin as the center of symmetry, while the Y element 14 is by itself point-symmetrically positioned with respect to the origin as the center of symmetry.

The single soft magnetic body 21 is formed in the shape of a button above the origin (that is to say, above the Y element 14), and the two soft magnetic bodies 22 are formed in the shape of a button in a substrate 11 and positioned at the ends of the X1 and X2 elements, which ends constitute two outer edges of the substrate 11 in the longitudinal direction, respectively.

The structure of the GSR elements 3 (hereafter referred to as "element structure") is described in reference to FIG. 3.

In the structure of the three elements 3, an amorphous wire (hereafter referred to as "wire") with a diameter of 10 μm is used at a length of 120 μm for the elements 12 and 13 for the x-axis, and at a length of 200 μm for the element 14 for the y-axis. A wire 31 is positioned in a central portion and surrounded by a detecting coil (hereafter referred to as "coil") 32 with an inner diameter of 20 μm and a coil pitch of 3 μm, containing 30 turns. To both ends of the wire 31 and the detecting coil 32, wire terminals 33 and coil terminals 35 are attached, respectively. Wire electrode pads 34 from the wire terminals 33 and coil electrode pads 36 from the detecting coil terminals 35 are used to correspond to integrated circuit terminals (not shown), respectively. The above respective terminals of each element 3 are electrically bonded to the respective terminals of the integrated circuit through the electrode pads.

Description is now made on the soft magnetic bodies 21 and 22.

The soft magnetic body 21 is formed above the origin of the substrate 11, with an insulating film being inserted between the body and the element 14, in the shape of a button with a diameter of 30 μm and a thickness of 30 μm that has the z-axis as the axis of its own. The soft magnetic body is formed by plating from a permalloy having a composition of 45 at % Ni—Fe.

The soft magnetic bodies 22 are each formed by providing the substrate 11 with an elliptical bore having a length of 80 μm, a width of 40 μm and a depth of 40 μm, and filling the bore by plating with a permalloy having a composition of 45 at %-Fe. The soft magnetic bodies as such are insulated from the elements 12 and 13, respectively.

For the soft magnetic bodies 21 and 22, a known soft magnetic material, such as pure Ni, pure iron, a permalloy having a composition other than the above, Sendust, and Permendur, may be used. The soft magnetic bodies may also be formed by, for instance, sputtering.

In the present example, two magnetic circuits in crank form are formed in the x-axial direction of the substrate 1. One circuit is composed of the X1 element 12 on the left side, which is positioned on the substrate 1, the soft magnetic body 22 on the left side, which is positioned below an end of the X1 element, and the soft magnetic body 21 above the origin. The other circuit is composed of the X2 element 13 on the right side, the soft magnetic body 22 on the right side, which is positioned below an end of the X2 element, and the soft magnetic body 21 above the origin.

The strength of the magnetic field in the z-axial direction is effectively detected by forming the two magnetic circuits in crank form symmetrically with respect to the origin.

The function of the magnetic circuits in crank form is described in reference to FIG. 2 (cross-sectional view taken along line A-A' in FIG. 1).

The magnetic field Hz in the z-axial direction magnetizes the two soft magnetic bodies 22 located at one end of the X1 element 12 and of the X2 element 13, respectively. If the magnetic pole at the bottom faces of the soft magnetic bodies 22 is a south pole, the magnetic pole at the top face of the soft magnetic body 21 above the origin will be a north pole. Each magnetic circuit 4 is formed in the form of a crank through the wire 31 of the element which is present between the relevant south pole and the north pole. In the magnetic circuit as formed, a strong magnetic field in proportion to the magnetic field Hz in the z-axial direction is caused to flow through the wire 31. An increased output is effectively attained by such formation of the magnetic circuits, which makes it possible to reduce the thickness of the soft magnetic body 21 above the origin to 0.03 mm. As a result, the height 16 of the three-dimensional magnetic field detection device 1 is specified to be 0.13 mm.

The outputs of the three GSR elements are separately measured. Arithmetic processing is performed to calculate the magnetic field strengths Hx, Hy and Hz in the x-axial, y-axial and z-axial directions using Equations (1), (2) and (3), where Hx1 represents the magnetic field strength of the X1 element 12, Hx2 represents the magnetic field strength of the X2 element 13, and Hy1 represents the magnetic field strength of the Y element 14. In Equation (3), K is a coefficient.

$$Hx = (Hx1 + Hx2) \quad (1)$$

$$Hy = Hy1 \quad (2)$$

$$Hz = K(Hx1 - Hx2) \quad (3)$$

The magnetic field strength in the x-axial direction is obtained from the value of addition of the outputs from the X1 element 12 and the X2 element 13. This is because the two elements form the magnetic circuits symmetrically in terms of a magnetic field component in the x-axial direction, and output values having a magnitude in proportion to the strength in the x-axial direction and being the same in sign.

With respect to the magnetic field strength in the y-axial direction, the output from the Y element 14 as a single element is considered to be the strength in the y-axial direction in itself.

The magnetic field strength in the z-axial direction is obtained from the difference between the outputs from the X1 element 12 and the X2 element 13. This is because the X1 element 12 and the X2 element 13 anti-symmetrically form magnetic circuits 6 in crank form, and the outputs from the two elements are in proportion to the magnetic field strength in the z-axial direction and opposite in sign.

Figure 5:
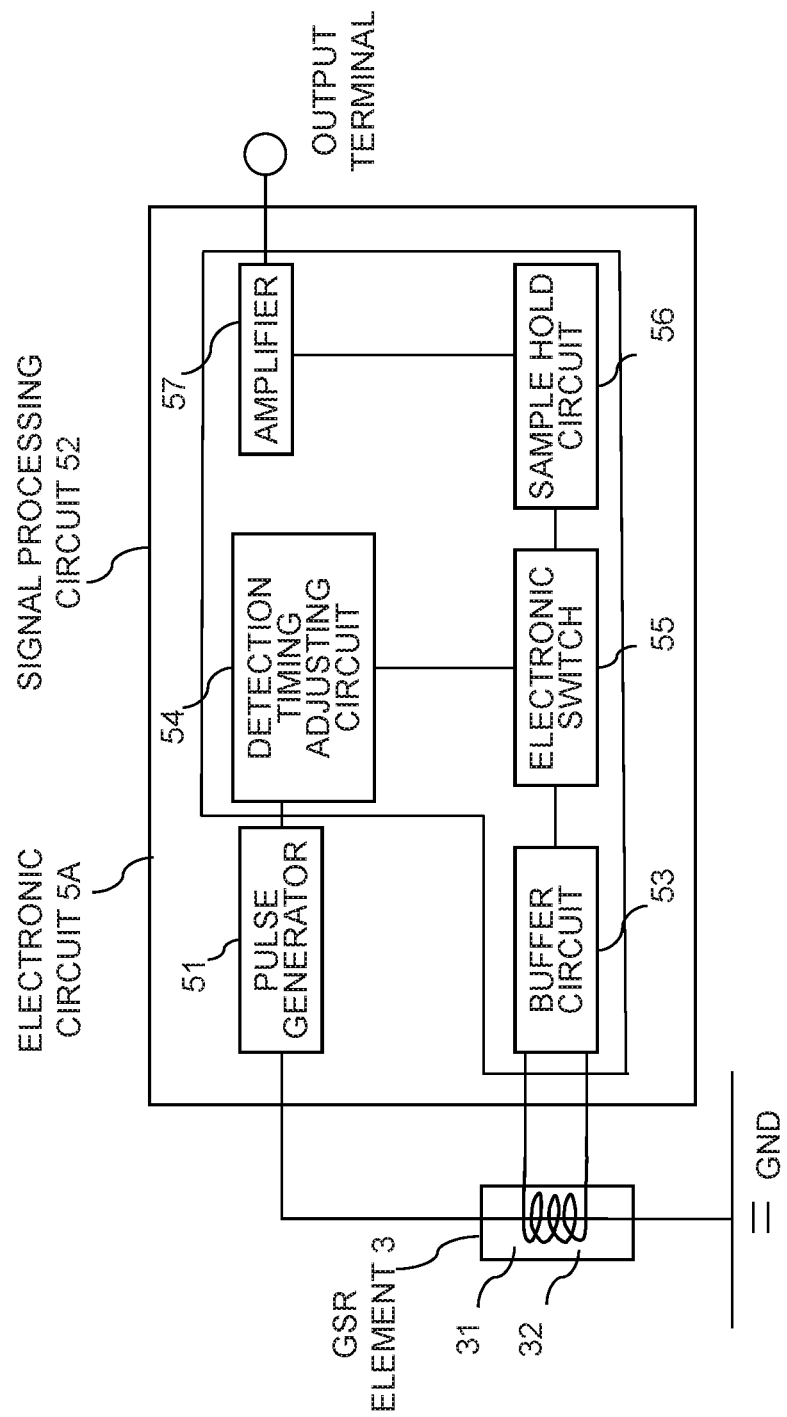
FIG. 5 is an electronic circuit diagram of a magnetic field detecting element according to Embodiment 1.
Figure 6:
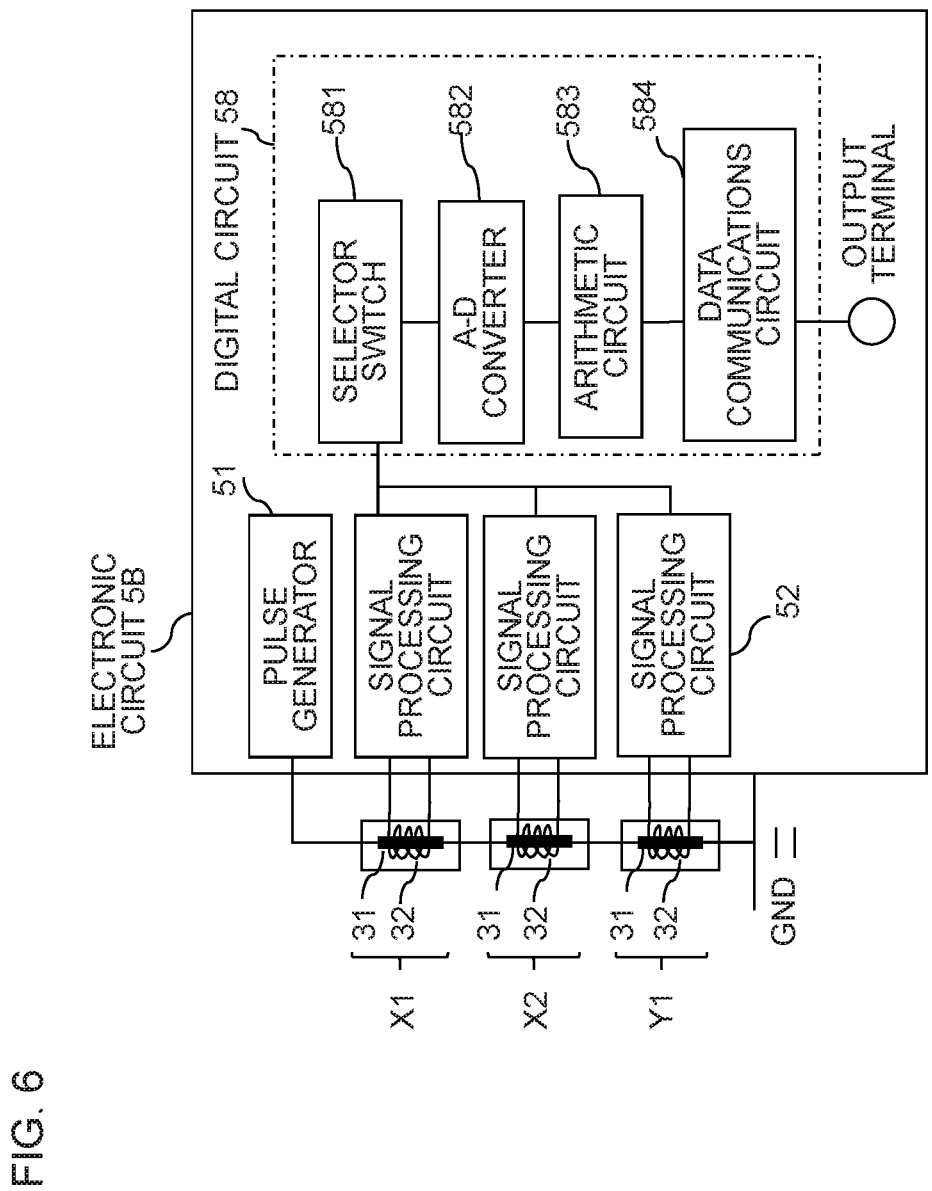
FIG. 6 is an electronic circuit diagram of the three-dimensional magnetic field detection device according to Embodiment 1.

The electronic circuit to be used in the three-dimensional magnetic field detection device of the present example is described in reference to FIGS. 5 and 6.

Initially, the basic operation of an electronic circuit 5A of a GSR sensor is illustrated referring to FIG. 5.

The electronic circuit 5A includes a pulse generating circuit (pulse generator) 51 and a signal processing circuit 52. The signal processing circuit 52 is composed of a buffer circuit 53, a detection timing adjusting circuit 54, an electronic switch 55, a sample hold circuit 56, and an amplifier 57. A pulsed current of a high frequency corresponding to 2 GHz that is generated by the pulse generating circuit 51 is fed to the wire 31 of a GSR element 3. Then, a magnetic field generated on the surface of the wire 31 by the pulsed current and an external magnetic field act on each other to generate a voltage corresponding to the external magnetic field on the coil 32. For convenience' sake, the pulse frequency as referred to herein is defined to be the reciprocal of the cycle of the pulsed current, with the cycle being assumed to last for a time four times as long as the "fall" time Δt of the pulsed current.

The output voltage from the coil 32 is input to the buffer circuit 53. The output voltage from the buffer circuit 53 is held as a capacitor voltage of the sample hold circuit 56 by a brief switching (on-off switching) of the electronic switch 55 by the detection timing adjusting circuit 54 at a specified timing after the fall of the pulsed current. The sampled voltage is amplified by the amplifier 57 and output.

Next, the function of an electronic circuit 5B of the present example that includes three GSR elements 3 is illustrated referring to FIG. 6.

The electronic circuit 5B includes a pulse generating circuit (pulse generator) 51, signal processing circuits 52, and a digital circuit 58. The pulse generating circuit (pulse generator) 51 is a single circuit, while the signal processing circuits 52 are three in number in order to measure the outputs of the respective elements at a time. The outputs from the three GSR elements (X1, X2 and Y1) are input to the digital circuit 58, sequentially converted into digital data by an A-D converter 582 using a selector switch 581, then transferred to an arithmetic circuit 583 to subject them to an appropriate arithmetic processing. Thus, the outputs are each converted into the strength of a three-dimensional vector. Subsequently, the strength values are transferred to a central processing unit controlling such a system as a smartphone through a data communications circuit 584.

The three-dimensional magnetic field detection device according to the present example is rectangular in shape, and has a length of 540 μm, a width of 250 μm, and a thickness of 120 μm including the thickness of the soft magnetic body above the origin. The three-dimensional magnetic field detection device as such is reduced in size to, for instance, one fourth of a three-dimensional magnetic field detection device in a square shape that is composed of four magnetic field detecting elements and three soft magnetic bodies.

Exemplified Embodiment 2

Figure 7:
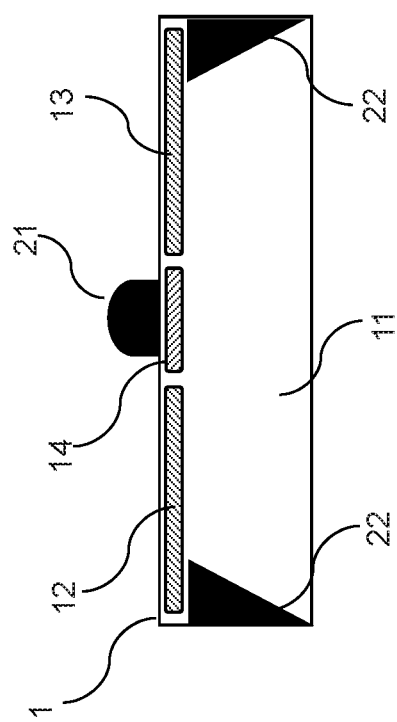
FIG. 7 is a cross-sectional view of a three-dimensional magnetic field detection device according to Embodiment 2, taken along line B-B' in the plan view (FIG. 1).

FIG. 7 is a cross-sectional view of a three-dimensional magnetic field detection device according to Example 2.

The three-dimensional magnetic field detection device of the present example is produced by cutting both end portions of the three-dimensional magnetic field detection device 1 of Example 1 (FIG. 1) along lines B-B'. The state of cut surfaces is shown in the cross-sectional view as taken along line A-A' in FIG. 1. The soft magnetic bodies in the end portions are each originally in the shape of an inverted cone, and have been subjected to cutting.

As a result of machining along line B-B' in the middle of the soft magnetic body 22 at an end of the X1 element 12 and along line B-B' in the middle of the soft magnetic body 22 at an end of the X2 element 13, the end faces of the soft magnetic bodies 22 appear on the left and right sides of the three-dimensional magnetic field detection device, respectively. The machining as above makes it possible to reduce the length of the three-dimensional magnetic field detection device. In the present example, the soft magnetic bodies 22 are partially removed by cutting along with the substrate 11, while the remaining parts thereof are adequate to maintain the magnetic circuits in crank form and, accordingly, the magnetic field detecting capability is in no way affected.

The three-dimensional magnetic field detection device according to the present example is reduced in size in the longitudinal direction by 50 μm at each end as compared with the device of Example 1, that is to say, has a length of 440 μm. The width of 250 μm and the thickness of 120 μm are kept unchanged. Therefore, a further reduction in size by about 20% is achieved.

EXPLANATION OF INDUSTRIAL APPLICABILITY OF THE INVENTION

The three-dimensional magnetic field detection device of the invention is necessary for a three-dimensional azimuth meter requiring three-dimensional terrestrial magnetism measurement, such as an electronic compass, a motion sensor and a smartphone. In particular, the three-dimensional magnetic field detector of the invention is suitable for an apparatus needing to be reduced in size and thickness in the direction perpendicular to a mounting substrate (so-called z-axial direction).

Furthermore, it is expected that, in the future, a three-dimensional magnetic field detector of a supermicro size is attached to the tip of a guide wire of a medical catheter, and a tip portion provided with the detector serves as a sensor for determining a three-dimensional position in the magnetic field space.

The invention claimed is:

1. A three-dimensional magnetic field detection device comprising magnetic field detecting elements configured to detect a magnetic field in a direction parallel to a face of a substrate and soft magnetic bodies configured to collect and radiate a magnetic field orthogonal to the face of the substrate, wherein:

an axis (X) extending in a first axial direction on the face of the substrate, an axis (Y) extending in a second axial direction orthogonal to the first axial direction, and an axis (Z) extending in a third axial direction orthogonal to the face of the substrate cross one another at an origin as a center of measurement of the magnetic field on the face of the substrate;

the magnetic field detecting elements are so arranged on the substrate that two of the magnetic field detecting elements are positioned in the first axial direction point-symmetrically with respect to the origin set as a center of symmetry and one of the magnetic field detecting elements is positioned in the second axial direction point-symmetrically with respect to the origin as the center of symmetry, and the soft magnetic bodies are positioned above the origin and below ends of the two of the magnetic field detecting elements positioned in the first axial direction, which ends are each opposite to the origin; and a magnetic circuit including the two of the magnetic field detecting elements and three of the soft magnetic bodies is formed in the first axial direction.

2. The three-dimensional magnetic field detection device according to claim 1, wherein two soft magnetic bodies positioned below the ends of two magnetic field detecting elements are each located on a surface of a machined end face machined in a direction perpendicular to the face of the substrate.

3. The three-dimensional magnetic field detection device according to claim 2, wherein the three-dimensional magnetic field detection device has a length of 0.6 mm or less, a width of 0.3 mm or less, and a thickness of 0.15 mm or less.

4. The three-dimensional magnetic field detection device according to claim 1, wherein the three-dimensional magnetic field detection device has a length of 0.6 mm or less, a width of 0.3 mm or less, and a thickness of 0.15 mm or less.

5. A three-dimensional magnetic field detector, comprising the three-dimensional magnetic field detection device according to claim 1 and an integrated circuit chip which is bonded to the three-dimensional magnetic field detection device.

6. A three-dimensional magnetic field detector according to claim 5, wherein the three-dimensional magnetic field detection device and the integrated circuit chip are electrically bonded together by stacking the three-dimensional magnetic field detection device and the integrated circuit chip to bond them to each other with a pad.

* * * * *